(12) United States Patent
Murad

(10) Patent No.: US 7,452,527 B2
(45) Date of Patent: Nov. 18, 2008

(54) METHODS OF PROMOTING HAIR GROWTH

(75) Inventor: Howard Murad, Marina del Ray, CA (US)

(73) Assignee: Murad, Inc., El Segundo, CA (US)

( * ) Notice: Subject to any disclaimer, the term of this patent is extended or adjusted under 35 U.S.C. 154(b) by 941 days.

(21) Appl. No.: 10/400,795

(22) Filed: Mar. 28, 2003

(65) Prior Publication Data
US 2004/0191202 A1 Sep. 30, 2004

(51) Int. Cl.
*A61Q 7/00* (2006.01)
(52) U.S. Cl. .................................................... 424/70.1
(58) Field of Classification Search ........................ None
See application file for complete search history.

(56) References Cited

U.S. PATENT DOCUMENTS

| | | | |
|---|---|---|---|
| 4,596,812 A | 6/1986 | Chidsey, III et al. ........ | 514/256 |
| 5,015,470 A * | 5/1991 | Gibson ........................... | 514/2 |
| 5,523,078 A | 6/1996 | Baylin ........................ | 424/70.1 |
| 5,597,575 A * | 1/1997 | Breitbarth ................... | 424/401 |
| 5,804,594 A | 9/1998 | Murad ........................ | 514/474 |
| 6,271,246 B1 * | 8/2001 | Murad ........................ | 514/356 |
| 6,465,514 B1 | 10/2002 | Hallam et al. ............... | 514/535 |
| 6,511,659 B2 | 1/2003 | Mahe et al. ................. | 424/70.1 |
| 6,838,252 B2 * | 1/2005 | Mundy et al. ................. | 435/23 |
| 2004/0171693 A1* | 9/2004 | Gan et al. ................... | 514/565 |

OTHER PUBLICATIONS

"The science of Hair Care" By Charles Zviak, Chapter 17, pp. 451-467 (1986).*

* cited by examiner

*Primary Examiner*—Jyothsna A Venkat
(74) *Attorney, Agent, or Firm*—Townsend and Townsend and Crew, LLP.

(57) ABSTRACT

The present invention relates to methods of promoting hair growth in a patient. The method comprises administering to a patient in need thereof a sugar compound that is converted to a glycosaminoglycan in the patient, a primary antioxidant component, at least one amino acid component, and one or more transition metals.

9 Claims, No Drawings

METHODS OF PROMOTING HAIR GROWTH

TECHNICAL FIELD OF THE INVENTION

The invention relates to methods of promoting hair growth in a patient in need thereof by administering to the patient a sugar compound that is converted to a glycosaminoglycan in the patient, a primary antioxidant component, at least one amino acid component, and one or more transition metals.

BACKGROUND

The human scalp normally harbors 100,000 to 150,000 hair follicles or hairs. The hair follicles or hair roots are the hair-forming organs. The long, strong, hairs, which build up the hair coverage of the head, are referred to as terminal hairs. The very fine, very short hairs, barely protruding over the surface of the skin, at the edges of the hair coverage on the head are referred to as fuzz hair, or vellus hair.

The growth of hair is not continuous, but cyclical. Three growth phases are identified: (1) the anagen phase, (2) the catagen phase, and (3) the telogen phase. The anagen phase is the period of active hair growth and, insofar as scalp hair is concerned, generally lasts from 3-5 years. The catagen phase is a short transitional phase between the anagen and the telogen phases, which, in the case of scalp hair, lasts only 1-2 weeks. The telogen phase is essentially a quiescent or resting phase where all growth ceases and the hair eventually is shed prior to the commencement of a new growth cycle. Scalp hair in the telogen phase is also relatively short-lived, some 3-4 months elapsing before the hair is shed and a new hair begins to grow. The hair of the head is thus under constant renewal. At any given time approximately 88% of the hairs are in the anagen phase, 1% are in the catagen phase, and the remainder are in the telogen phase.

Dermatologists recognize many different types of hair loss, the most common by far being "alopecia," or male pattern baldness, in which humans, typically males, begin losing scalp hair at the temples and on the crown of the head as they get older. While this kind of hair loss is largely confined to males, it is not unknown in women. Other types of hair loss, which can be considerable, temporary or permanent, can be induced by poor nutrition; emotional stress; hormone imbalance; or medicinal drugs, such as cancer chemotherapy agents. These disorders and the mechanisms that produce them are poorly understood. Nevertheless, they are common and distressing, since hair is an important factor in human social and sexual communication.

U.S. Pat. No. 4,596,812 to Chidsey III et al. discloses a method for treating alopecia which comprises regular topical application of the compound 2,4-diamino-6-piperidino-pyrimidine 3-oxide or "Minoxidil."

U.S. Pat. No. 5,523,078 to Baylin discloses an aqueous composition for the treatment of hair and scalp which includes a chelating agent, gellan gum, a vitamin precursor, a preservative, biotin, a vitamin derivative, gamma-linolenic acid, menthol, a liposome, a conditioner, a solubilizer, a conditioner/humectant, folic acid, and a poly amino sugar condensate.

U.S. Pat. No. 6,465,514 to Hallam discloses compositions consisting essentially of procaine hydrochloride, niacin and minoxidil. The compositions are allegedly useful for promoting hair growth.

U.S. Pat. No. 6,511,659 to Mahe et al. discloses pyrimidine 3-oxide compounds allegedly useful for inducing/stimulating hair growth or retarding hair loss.

U.S. Pat. No. 6,271,246 to Murad discloses pharmaceutical compositions consisting essentially of an acidic component comprising a hydroxy acid or tannic acid, a niacin component, and a 5-α reductase inhibitor. The compositions are useful for managing scalp conditions such as thinning hair.

U.S. Pat. No. 5,804,594 to Murad discloses pharmaceutical compositions useful for improving wrinkles and other skin conditions. The compositions include a sugar compound that is converted to glycosaminoglycan in the patient, a primary antioxidant component, at least one amino acid component, and at least one transition metal component.

Despite attempts in the pharmaceutical and cosmetic industry to develop compositions to promote hair growth and reduce alopecia, no widely accepted solution exists. Moreover, many of the proposed solutions present unwanted side effects. Hence, there is still a need for effective and safe compositions to promote hair growth.

SUMMARY OF THE INVENTION

The present invention relates to methods of promoting hair growth in a patient in need thereof. The method comprises administering to the patient (i) a sugar compound that is converted to a glycosaminoglycan in the patient, (ii) a primary antioxidant component, (iii) at least one amino acid component, and (iv) at least one transition metal component.

DETAILED DESCRIPTION

Applicants have discovered that administering to a patient (i) a sugar compound that is converted to a glycosaminoglycan in the patient, (ii) a primary antioxidant component, (iii) at least one amino acid, and (iv) at least one transition metal component (collectively "the hair growth components") promotes hair growth in the patient.

In one embodiment, the patient is a mammal. In another embodiment, the patient is a human.

The method involves administering a sugar compound that is converted to a glycosaminoglycan in the patient. In one embodiment, the sugar compound is N-acetyl glucosamine, D-glucosamine sulfate, or chondroitin sulfate. In a preferred embodiment, the sugar compound is a pharmaceutically acceptable salt or ester of N-acetylglucosamine. In a more preferred embodiment, the sugar compound is N-acetylglucosamine itself. Typically, the daily dose of the sugar component is from about 40 mg to about 2500 mg per day, preferably from about 60 mg to about 1000 mg per day, and more preferably from about 100 mg to about 300 mg per day.

The primary antioxidant is typically a vitamin C source. Preferably, the primary antioxidant is ascorbic acid, or a pharmaceutically acceptable salt or ester thereof, and more preferably is ascorbyl palmitate; dipalmitate L-ascorbate; sodium L-ascorbate-2-sulfate; or an ascorbate salt, such as sodium, potassium, or calcium ascorbate; or mixtures thereof. Typically, the daily dose of the primary antioxidant source is from about 40 mg to about 2400 mg per day, preferably from about 60 mg to about 600 mg per day, and more preferably from about 80 to about 300 mg per day. Vitamin C, the typical primary antioxidant for the method, is approved by the FDA and has wide consumer acceptance, so that it can be used in amounts as high as 10,000 mg, if desired. When oral formulations of the pharmaceutical composition are used, it is preferred that a non-acidic form of vitamin C be used to reduce stomach irritation that may occur when using an acidic form.

The method also involves administering at least one amino acid. Preferably, two or more amino acids are administered in combination. Either the L- or D-forms of amino acids are acceptable. Lysine and proline are the most preferred amino acids and are advantageously used in combination. Cysteine, methionine or other amino acids can also be used, if desired. A useful source of the amino acid cysteine is N-acetyl cysteine and a useful source of the amino acid methionine is L-selenomethionine, wherein the selenium component is between about 0.1 to about 3 weight percent of the methionine source. The amino acids may be administered in a soluble form such as a salt, for example, a hydrochloride salt such as L-Lysine hydrochloride. Typically, the daily dose for each amino acid is from about 35 mg per day to about 1200 mg per day, preferably from about 50 mg per day to about 600 mg per day, and more preferably from about 70 mg per day to about 400 mg per day.

The method also involves administering one or more transition metals. Preferably the transition metal is zinc, manganese, copper, or combinations thereof. The combinations are most preferred. Typically, the daily dose of the transition metal component is from about 4.1 mg to about 740 mg per day, more preferably from about 8.2 mg to about 370 mg per day, and most preferably from about 20 mg to about 150 mg per day. In one embodiment, the one or more transition metals are a combination of zinc and manganese. In another embodiment, the one or more transition metals are a combination of zinc and copper. In another embodiment, the one or more transition metals are a combination of manganese and copper. In another embodiment, the one or more transition metals are a combination of zinc, manganese, and copper.

When the transition metal comprises zinc, the zinc may be any zinc compound or pharmaceutically acceptable salt thereof. In one embodiment, the zinc is complexed with an amino acid. In one embodiment, the zinc is present as zinc monomethionine, wherein the zinc is present in an amount of from about 10 to about 30 weight percent of the complex.

When the transition metal comprises manganese, the manganese may be any manganese compound or pharmaceutically acceptable salt thereof. In one embodiment, the manganese is at least partially complexed with a vitamin C source, wherein the manganese is present in an amount of from about 5 to 20 weight percent of the complex. When complexed with vitamin C, the vitamin C source may be included in the overall percentage of vitamin C used as the primary antioxidant in the method. In one embodiment, the manganese is present as manganese ascorbate or manganese ascorbic acid.

When the transition metal comprises copper, the copper may be any copper compound or pharmaceutically acceptable salt thereof. In one embodiment, the copper is present as copper sebacate, wherein the copper is present in an amount of from about 5 to about 20 weight percent of the copper sebacate.

In one embodiment, the hair growth components are administered sequentially.

In another embodiment, the hair growth components are administered concurrently, for example as a composition comprising each of the hair growth components.

When the hair growth components are administered sequentially, the time span between the administration of each ingredient typically ranges from about 1 minute to about 1 day. In this embodiment, the hair growth components can be administered in any order.

When the hair growth components are administered concurrently, they can be administered as a composition ("the hair growth composition") that comprises each of the sugar compound that is converted to a glycosaminoglycan in the patient, the primary antioxidant component, the at least one amino acid, and the transition metal component. In one embodiment, the hair growth composition may be administered as a single dose once per day. In another embodiment, the dose is divided and administered from about 1 to about 10 times per day, preferably about 2 to 6 times per day, and more preferably about 4 times per day. The term "dose" is meant to describe a daily dose.

The sugar compound that is converted to a glycosaminoglycan in the patient is typically present in the hair growth composition in an amount of from about 5 to about 50 weight percent, preferably from about 10 to about 40 weight percent, and more preferably from about 15 to about 30 weight percent of the hair growth composition.

The primary antioxidant component is typically present in the hair growth composition in an amount of from about 5 to about 50 weight percent, preferably from about 7 to about 40 weight percent, and more preferably from about 10 to about 25 weight percent the hair growth composition.

The one or more amino acids are each typically present in the hair growth composition in an amount of from about 2 to about 25 weight percent, preferably from about 4 to about 20 weight percent, and more preferably from about 6 to about 15 weight percent of the hair growth composition. When the amino acid source is a cysteine source, such as N-acetyl cysteine, it is typically present in the hair growth composition in an amount of from about 1 to about 10 weight percent, preferably from about 2 to about 8 weight percent, and more preferably from about 3 to about 6 weight percent of the hair growth composition. When the amino acid source is a methionine source, such L-selenomethionine, it is typically present in the hair growth composition in an amount of from about 0.1 to about 5 weight percent, preferably from about 0.2 to about 3 weight percent, and more preferably from about 0.3 to about 1 weight percent of the hair growth composition.

The transition metal components are present in the hair growth composition in an amount of from about 0.5 to about 15 weight percent of the hair growth composition. When the transition metal is zinc, the zinc is typically present in an amount of from about 1 to about 10 weight percent, more preferably about 2 to about 7 weight percent and most preferably about 3 to about 5 weight percent of the hair growth composition. When the transition metal is manganese, the manganese is typically present in the hair growth composition in an amount of from about 1 to about 10 weight percent, preferably about 2 to about 7 weight percent, and more preferably about 2.5 to about 4 weight percent of the hair growth composition. When the transition metal is copper, the copper is typically present in the hair growth composition in an amount of from about 0.1 to about 5 weight percent, preferably about 0.2 to about 3 weight percent, and more preferably about 0.3 to about 1 weight percent of the hair growth composition.

The term "pharmaceutically acceptable salt", as used herein, refers to a salt prepared from pharmaceutically acceptable non-toxic acids or bases including inorganic or organic acids. Examples of such inorganic acids are hydrochloric, hydrobromic, hydroiodic, sulfuric, and phosphoric. Appropriate organic acids may be selected, for example, from aliphatic, aromatic, carboxylic and sulfonic classes of organic acids, examples of which are formic, acetic, propionic, succinic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic, stearic, sulfanilic, algenic, and galacturonic. Examples of such inorganic bases, for potential salt formation with the sulfate or phosphate compounds of the invention, include metallic salts made from aluminum, calcium, lithium, magnesium, potassium, sodium, and zinc.

Appropriate organic bases may be selected, for example, from N,N-dibenzylethylenediamine, chloroprocaine, choline, diethanolamine, ethylenediamine, meglumaine (N-methylglucamine), and procaine.

In addition to the hair growth components, the method of the invention may further involve administering one or more optional additives. In one embodiment, the method further involves administering a catechin-based preparation, along with glucosamine or a pharmaceutically acceptable salt or ester thereof, and chondroitin or a pharmaceutically acceptable salt or ester thereof.

The catechin-based preparation is preferably a proanthanol or proanthocyanidin, more preferably a proanthocyanidin, and most preferably grape seed extract. These compounds are considered to be secondary antioxidants, because they are present in lesser amounts than the primary antioxidant. A daily dose of the catechin-based preparation is typically from about 5 mg to about 2250 mg per day, more preferably from about 7.5 mg to about 500 mg per day, and most preferably from about 10 mg to about 50 mg per day. When the catechin-based preparation is included in the hair growth composition, the catechin-based preparation is typically present in an amount of from about 0.5 to about 5 weight percent, more preferably from about 0.6 to about 3 weight percent, and most preferably from about 0.7 to about 2 weight percent of the hair growth composition.

The typical dose for the glucosamine or a pharmaceutically acceptable salt or ester thereof is from about 10 mg to about 1500 mg per day, more preferably from about 50 to about 750 mg per day, and most preferably from about 100 to about 200 mg per day. The typical dose for the chondroitin or a pharmaceutically acceptable salt or ester thereof is from about 10 mg to about 1500 mg per day, more preferably from about 50 to about 750 mg per day, and most preferably from about 100 to about 200 mg per day. When the glucosamine or a pharmaceutically acceptable salt or ester thereof and the chondroitin or a pharmaceutically acceptable salt or ester thereof are included in the hair growth composition, the glucosamine or a pharmaceutically acceptable salt or ester thereof, and the chondroitin or a pharmaceutically acceptable salt or ester thereof are each typically present in an amount of from about 3 to about 17 weight percent, preferably from about 4 to about 12 weight percent each, and more preferably from about 5 to about 8 weight percent of the hair growth composition. In one embodiment, the glucosamine or a pharmaceutically acceptable salt or ester thereof is present as a sulfate or succinate; preferably as D-glucosamine sulfate, wherein the glucosamine is present as about 60 to about 90 weight percent of the salt. In another embodiment, the chondroitin is present as a sulfate or succinate; preferably as chondroitin sulfate, wherein the chondroitin is present as about 65 to about 95 weight percent of the salt.

The method may further involve administering one or more optional additives such as a vitamin E source, a vitamin $B_3$ source, quercetin powder, pyridoxal 5 phosphate-Co $B_6$, or a vitamin A source.

In one embodiment, the method further involves administering a vitamin E source. In one embodiment, the vitamin E source is a sulfate or succinate vitamin E complex. In another embodiment, the vitamin E source is D-alpha tocopheryl acid succinate. The dose for any of these vitamin E sources is typically from about 10 mg to about 800 mg per day, more preferably from about 25 mg to about 400 mg per day, and most preferably from about 40 mg to about 120 mg per day. The vitamin E source, however, should not be ingested in an amount higher than about 1,500 mg per day, as Vitamin E becomes toxic at higher doses. When the vitamin E source is included as part of the hair growth composition, the vitamin E source is typically present in an amount of from about 1 to about 15 weight percent, preferably from about 2 to about 12 weight percent, and more preferably from about 3 to about 10 weight percent of the hair growth composition.

In one embodiment, the method further involves administering a vitamin $B_3$ source. The dose for any vitamin $B_3$ source is typically from about 4 mg to about 125 mg per day, preferably from about 10 mg to about 75 mg per day, and more preferably from about 20 mg to about 50 mg per day. In one embodiment, the vitamin $B_3$ source is niacinamide. When the vitamin $B_3$ source is included as part of the hair growth composition, the vitamin $B_3$ source is typically present in an amount of from about 0.5 to about 15 weight percent, preferably from about 1 to about 12 weight percent, and more preferably from about 1.5 to about 10 weight percent of the hair growth composition.

In one embodiment, the method further involves administering a vitamin A source. In one embodiment, the vitamin A dose is about 500,000 IU (or 165 mg) per day. Vitamin A is toxic at high levels, such that no more than 400,000 IU should be cumulatively ingested per day for greater than six months. Preferably, the dose for any Vitamin A compound is from about 2 mg to about 20 mg per day, and more preferably from about 4 mg to about 10 mg per day. In one embodiment, the vitamin A source is vitamin A palmitate. When the vitamin A source is included in the hair growth composition, the vitamin A source is typically present in an amount of from about 0.1 to about 5 weight percent, preferably from about 0.2 to about 3 weight percent, and more preferably from about 0.3 to about 1 weight percent of the hair growth composition.

In one embodiment, the method further involves administering quercetin powder. The dose for quercetin powder is typically from about 4 mg to about 125 mg per day, more preferably from about 10 mg to about 75 mg per day, and most preferably from about 20 mg to about 50 mg per day. In one embodiment, the quercitin powder is quercetin dihydrate. When quercitin powder is included as part of the hair growth composition it is typically present in an amount of from about 0.5 to about 15 weight percent, preferably from about 1 to about 12 weight percent, and more preferably from about 1.5 to about 10 weight percent of the hair growth composition.

In one embodiment, the method further involves administering pyridoxal 5 phosphate-Co $B_6$, also known as P-5-P monohydrate. The dose for pyridoxal 5 phosphate-Co $B_6$ is typically from about 1 mg to about 40 mg per day, more preferably from about 2 mg to about 20 mg per day, and most preferably from about 4 mg to about 10 mg per day. When the pyridoxal 5 phosphate-Co $B_6$ is included as part of the hair growth composition it is typically present in an amount of from about 0.1 to 5 weight percent, preferably from about 0.2 to 3 weight percent, and more preferably from about 0.3 to 1 weight percent of the hair growth composition.

In one embodiment, the method further involves administering one or more of lecithin, phosphatidyl choline, or choline. The dose for lecithin is typically from about 10 mg to about 25,000 mg per day, more preferably from about 25 mg to about 15,000 mg per day, and most preferably from about 50 mg to about 1,000 mg per day. When lecithin is included as part of the hair growth composition it is typically present in an amount of from about 0.5 to about 75 weight percent, preferably from about 1.0 to about 50 weight percent, and more preferably from about 1.5 to about 20 weight percent of the hair growth composition. The dose for phosphatidyl choline is typically from about 1 mg to about 10,000 mg per day, more preferably from about 10 mg to about 5,000 mg per day, and most preferably from about 20 mg to about 500 mg per day.

When phosphatidyl choline is included as part of the hair growth composition it is typically present in an amount of from about 0.5 to about 50 weight percent, preferably from about 1.0 to about 25 weight percent, and more preferably from about 1.5 to about 10 weight percent of the hair growth composition. The dose for choline is typically from about 0.5 mg to about 3,000 mg per day, more preferably from about 1 mg to about 500 mg per day, and most preferably from about 2 mg to about 50 mg per day. When choline is included as part of the hair growth composition it is typically present in an amount of from about 0.5 to about 25 weight percent, preferably from about 1.0 to about 10 weight percent, and more preferably from about 1.5 to about 5 weight percent of the hair growth composition. Without wishing to be bound by theory, Applicants believe that the combination of glycosaminoglycan and one or more of lecithin, phosphatidyl choline, or choline strengthens the cell membrane and increases the water content of cells which improves hair growth.

In one embodiment, the method involves topical administration and further includes administering hydrogen peroxide. The hydrogen peroxide is administered in an amount sufficient to cleanse at least a portion of the skin. Preferably, the hydrogen peroxide is administered in an amount to cleanse the skin without substantial irritation. "Cleanse", as used herein, includes the removal of dirt, debris, air pollutants, desquamating cells, and cutaneous secretions of the skin. In one embodiment, the hydrogen peroxide is topically administered as a 3% solution (by mass) to cleanse the skin before topically administering the hair growth components. When the hydrogen peroxide is included as part of the hair growth composition it is typically present in an amount of from about 0.01 to about 6 weight percent, preferably from about 0.05 to about 4 weight percent, and more preferably from about 0.1 to about 1 weight percent of the hair growth composition. Without wishing to be bound by theory it is believed that cleansing the skin with hydrogen peroxide improves penetration into the skin of the topically applied hair growth components.

In one embodiment, the method involves topical administration and further includes administering to the patient one or more moisturizing agents. "Moisturizing agent," as used herein, is used to include any agent that facilitates hydration of the skin by inhibiting or preventing loss of water from the skin, absorbing water from the atmosphere and hydrating the skin, or enhancing the skin's own ability to absorb water directly from the atmosphere, or a combination thereof. Preferably, when the method involves administering a moisturizing agent, the moisturizing agent and the hair growth components are administered topically. Without wishing to be bound by theory it is believed that the moisturizing agent improves the skin's ability to absorb topically administered hair growth components. Moisturizing agents also minimize or prevent the skin from drying and cracking; cracked skin is more susceptible to environmental factors that generate free radicals, which are believed to damage the skin. Suitable moisturizing agents include, but are not limited to, hydrophobic agents, and hydrophilic agents, and combinations thereof. The dose for any of these moisturizing agents is typically from about 0.1 mg to about 2000 mg per day, preferably from about 1 mg to about 500 mg per day, and more preferably from about 5 mg to about 100 mg per day. When the moisturizers are included as part of the hair growth composition, the total amount of moisturizers are typically present in an amount of from about 0.01 to about 20 weight percent, preferably from about 0.05 to about 10 weight percent, and more preferably from about 0.1 to about 5 weight percent of the hair growth composition.

Representative moisturizing agents that are hydrophobic moisturizing agents include, but are not limited to, ceramide, borage oil (linoleic acid), tocopherol (Vitamin E), tocopherol linoleate, dimethicone, glycerine, and mixtures thereof. Hydrophobic agents, when present, are believed to moisturize the skin by inhibiting or preventing the loss of water from the skin. The hydrophobic agent, when present in the hair growth composition, is typically present in an amount of from about 0.01 to about 20 weight percent, preferably from about 0.05 to about 15 weight percent, and more preferably from about 0.1 to about 5 weight percent of the hair growth composition.

Representative moisturizing agents that are hydrophilic agents include, but are not limited to, hyaluronic acid, sodium peroxylinecarbolic acid (sodium PCA), wheat protein (e.g., laurdimonium hydroxypropyl hydrolyzed wheat protein), hair keratin amino acids, and mixtures thereof. Sodium chloride may also be present, particularly when hair keratin amino acids are included as a moisturizer. Hydrophilic agents, when present, are believed to moisturize the skin by absorbing moisture from the atmosphere to hydrate or facilitate hydration of the skin. The hydrophilic agent, when present in the hair growth composition, is typically present in an amount of from about 0.01 to about 20 weight percent, preferably from about 0.05 to about 15 weight percent, and more preferably from about 0.1 to about 5 weight percent of the hair growth composition.

Other moisturizing agents that hydrate the skin and are useful in the compositions and methods of the present invention include, but are not limited to, panthenol; primrose oil; GLA 3 and other fish oils that may include, for example, the omega-3 and omega-6 oils and/or linoleic acid; and flax seed oil.

In one embodiment, the method involves administering both a hydrophilic moisturizing agent and a hydrophobic moisturizing agent. Without wishing to be bound by theory it is believed that the combination of a hydrophilic moisturizing agent and a hydrophobic moisturizing agent interact in a synergistic manner to provide optimum conditions for absorption by the skin of topically applied hair growth components.

In another embodiment, the method involves topical administration of the hair growth components and further includes administering an exfoliant to help remove dead or dying skin cells and further improve the skin's own ability to absorb the hair growth components. In another embodiment, the method involves topical administration of the hair growth components in combination with an exfoliant and one or more moisturizing agents. Preferably, the method involves topical administration of the hair growth components in combination with an exfoliant, a hydrophilic moisturizing agent, and a hydrophilic moisturizing agent. Without wishing to be bound by theory it is believed that the combination of an exfoliant, a hydrophilic moisturizing agent, and a hydrophobic moisturizing agent interact in a synergistic manner to provide optimum conditions for absorption by the skin of topically applied hair growth components.

The exfoliant may be an enzymatic exfoliant, or an acidic exfoliant. Any enzymatic exfoliant known to those skilled in the art may be used in the compositions and methods of the invention. Examples of enzymatic exfoliants useful in the compositions and methods of the invention include, but are not limited to, papain, from papaya, and bromalein, from pineapple.

Examples of acidic exfoliants include, but are not limited to a mono- or poly-hydroxy acid, tannic acid, or a mixture thereof, or a pharmaceutically acceptable salt or ester thereof. One of ordinary skill in the art will be readily able to select and prepare suitable mono- or poly-hydroxy acids for use in the composition of the invention, for example, alkyl hydroxycarboxylic acids, aralkyl and aryl hydroxycarboxylic acids, polyhydroxy-carboxylic acids, and hydroxy-polycarboxylic acids. One of ordinary skill in the art would typically select one or more of the following mono- or poly-hydroxy acids: 2-hydroxyacetic acid (glycolic acid); 2-hydroxypropanoic acid (lactic acid); 2-methyl 2-hydroxypropanoic acid; 2-hydroxybutanoic acid; phenyl 2-hydroxyacetic acid; phenyl 2-methyl 2-hydroxyacetic acid; 3-phenyl 2-hydroxyacetic acid; 2,3-dihydroxypropanoic acid; 2,3,4-trihydroxybutanoic acid; 2,3,4,5,6-pentahydroxyhexanoic acid; 2-hydroxydodecanoic acid; 2,3,4,5-tetrahydroxypentanoic acid; 2,3,4,5,6,7-hexahydroxyheptanoic acid; diphenyl 2-hydroxyacetic acid; 4-hydroxymandelic acid; 4-chloromandelic acid; 3-hydroxybutanoic acid; 4-hydroxybutanoic acid; 2-hydroxyhexanoic acid; 5-hydroxydodecanoic acid; 12-hydroxydodecanoic acid; 10-hydroxydecanoic acid; 16-hydroxyhexadecanoic acid; 2-hydroxy-3-methylbutanoic acid; 2-hydroxy-4-methylpentanoic acid; 3-hydroxy-4-methoxymandelic acid; 4-hydroxy-3-methoxymandelic acid; 2-hydroxy-2-methylbutanoic acid; 3-(2-hydroxyphenyl) lactic acid; 3-(4-hydroxyphenyl) lactic acid; hexahydromandelic acid; 3-hydroxy-3-methylpentanoic acid; 4-hydroxydecanoic acid; 5-hydroxydecanoic acid; aleuritic acid; 2-hydroxypropanedioic acid; 2-hydroxybutanedioic acid; erythraric acid; threaric acid; arabiraric acid; ribaric acid; xylaric acid; lyxaric acid; glucaric acid; galactaric acid; mannaric acid; gularic acid; allaric acid; altraric acid; idaric acid; talaric acid; 2-hydroxy-2-methylbutanedioic acid; citric acid, isocitric acid, agaricic acid, quinic acid, glucoronic acid, glucoronolactone, galactoronic acid, galactoronolactone, uronic acids, uronolactones, ascorbic acid, dihydroascorbic acid, dihydroxytartaric acid, tropic acid, ribonolactone, gluconolactone, galactonolactone, gulonolactone, mannonolactone, citramalic acid; pyruvic acid, hydroxypyruvic acid, hydroxypyruvic acid phosphate and esters thereof; methyl pyruvate, ethyl pyruvate, propyl pyruvate, isopropyl pyruvate; phenyl pyruvic acid and esters thereof; methyl phenyl pyruvate, ethyl phenyl pyruvate, propyl phenyl pyruvate; formyl formic acid and esters thereof; methyl formyl formate, ethyl formyl formate, propyl formyl formate; benzoyl formic acid and esters thereof; methyl benzoyl formate, ethyl benzoyl formate and propyl benzoyl formate; 4-hydroxybenzoyl formic acid and esters thereof; 4-hydroxyphenyl pyruvic acid and esters thereof; and 2-hydroxyphenyl pyruvic acid and esters thereof.

In one embodiment the poly-hydroxy acidic components is an alpha-hydroxy acid. Preferred alpha-hydroxy acids include citric acid, glycolic acid, lactic acid. In another embodiment the poly-hydroxy acidic exfoliant is a beta-hydroxy acid. A preferred beta-hydroxy acid is salicylic acid.

It should be understood that one or more derivatives of the above acidic component, such as esters or lactones thereof, are also suitably used. One of ordinary skill in the art will also understand that various hydroxy acids described in U.S. Pat. Nos. 5,547,988 and 5,422,370 are also suitable for use in the compositions and methods of the invention. The acidic component is present in the hair growth composition in an amount sufficient to exfoliate, i.e., remove dead or dying skin cells, from at least a portion of the skin. The acidic component, when included in the hair growth composition, is typically present in an amount of from about 0.1 to 12 weight percent, preferably from about 1 to 11 weight percent, more preferably from about 4 to 10 weight percent of the hair growth composition. In one embodiment, the acidic component is citric acid in an amount of from about 0.1 to 3 weight percent of the hair growth composition in combination with salicylic acid in an amount of up to about 2 weight percent of the hair growth composition.

Any route of administration can be used in the method of the invention. Suitable routes of administration include, but are not limited to, oral, topical rectal, parenteral, intravenous, transdermal, subcutaneous, and intramuscular. Although the method includes any suitable route of administration for providing the patient with an effective dosage of the hair growth components, topical and oral administration are preferred. Suitable dosage forms include tablets, troches, dispersions, suspensions, solutions, capsules, patches, suppositories, and the like, although oral and topical dosage forms are preferred.

It should be understood that the magnitude of a prophylactic or therapeutic dose of the composition in the promotion of hair growth will vary with the severity of the condition to be treated and the route of administration. The dose, and perhaps the dose frequency, will also vary according to the age, body weight, and response of the individual patient.

It is further recommended that children, patients aged over 65 years, and those with impaired renal or hepatic function initially receive low doses, and that they then be titrated based on individual response(s) or blood level(s). It may be necessary to use dosages outside the suggested ranges in some cases, as will be apparent to those of ordinary skill in the art. Further, it is noted that the clinician or treating physician will know how and when to interrupt, adjust, or terminate therapy in conjunction with individual patient response.

The compositions used in the methods of the present invention include the hair growth components and may also include pharmaceutically acceptable carriers, excipients and the like, and optionally, other therapeutic ingredients.

The hair growth compositions for use in the methods of the present invention include compositions such as suspensions, solutions and elixirs; aerosols; or carriers such as starches, sugars, microcrystalline cellulose, diluents, granulating agents, lubricants, binders, disintegrating agents, and the like, in the case of oral solid preparations (such as powders, capsules, and tablets), with the oral solid preparations being preferred over the oral liquid preparations. The most preferred oral solid preparations are tablets.

In one embodiment, the method involves oral administration of the hair growth components. Because of their ease of administration, tablets and capsules represent the most advantageous oral dosage unit form, in which case solid pharmaceutical carriers are employed. If desired, tablets may be coated by standard aqueous or nonaqueous techniques.

Pharmaceutical compositions for use in the methods of the present invention suitable for oral administration may be presented as discrete units such as capsules, cachets, or tablets, or aerosol sprays, each containing a predetermined amount of the active ingredient, as a powder or granules, as creams, pastes, gels, or ointments, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the carrier with the active ingredient which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent. Desirably, each tablet, cachet or capsule, contains from about 1 mg to 4,000 mg of the hair growth components, preferably about 200 mg to 3,000 mg of the hair growth components, and more preferably about 600 mg to 2,000 mg of the of the hair growth components.

In another embodiment, the method involves topical administration of the hair growth components.

Suitable dosage forms for topical administration of the hair growth composition include, but are not limited to, dispersions; lotions; creams; gels; pastes; powders; aerosol sprays; syrups or ointments on sponges or cotton applicators; and solutions or suspensions in an aqueous liquid, non-aqueous liquid, oil-in-water emulsion, or water-in-oil liquid emulsion. Because of its ease of administration, a cream, lotion, or ointment represents the most advantageous topical dosage form, in which case liquid pharmaceutical carriers may be employed in the composition. These creams, lotions, or ointments, may be prepared as rinse-off or leave-on products, as well as two stage treatment products for use with other skin cleansing or managing compositions. In one embodiment, the hair growth compositions are administered as a rinse-off product in a higher concentration form, such as a gel, and then a leave-on product in a lower concentration to avoid irritation of the skin. Each of these forms is well understood by those of ordinary skill in the art, such that dosages may be easily prepared to incorporate the hair growth components of the invention.

In addition to the common dosage forms set out above, the compound for use in the methods of the present invention may also be administered by controlled release means and/or delivery devices such as those described in U.S. Pat. Nos. 3,845,770; 3,916,899; 3,536,809; 3,598,123; and 4,008,719, the disclosures of which are hereby incorporated by reference.

The hair growth compositions used in the methods of the invention may be prepared by any of the methods of pharmacy, but all methods include the step of bringing into association the carrier(s) with the active ingredient, which constitutes one or more necessary ingredients. In general, the hair growth compositions are prepared by uniformly and intimately admixing the active ingredient with liquid carriers or finely divided solid carriers or both, and then, if necessary, shaping the product into the desired presentation.

In another embodiment of the invention, the hair growth components can be administered to the patient along with a second hair growth agent. In one embodiment, the second hair growth agent is selected from minoxidil, procaine hydrochloride, niacin, pyrimidine 3-oxide compounds, or mixtures thereof.

EXAMPLES

The invention is further defined by reference to the following examples describing in detail the preparation of hair growth compositions useful in the methods of the invention, as well as their utility. The examples are representative, and they should not be construed to limit the scope of the invention.

Example 1

Capsules

A large number of unit capsules are prepared by filling standard two-piece hard gelatin capsules each with the desired amount of powdered hair growth components, 150 milligrams of lactose, 50 milligrams of cellulose, and 6 milligrams magnesium stearate.

Example 2

Soft Gelatin Capsules

A mixture of hair growth components in a digestible oil such as soybean oil, lecithin, cottonseed oil or olive oil is prepared and injected by means of a positive displacement pump into gelatin to form soft gelatin capsules containing the desired amount of the hair growth components. The capsules are washed and dried for packaging.

Example 3

Tablets

A large number of tablets were prepared by conventional procedures so that the tablet unit included: the desired amount of the hair growth components as described herein, 50 milligrams of red beet root powder, 12 milligrams of stearic acid, 10.95 milligrams of sorbitol, 3 milligrams of acdisol, 1 milligram of magnesium stearate, and 1 milligram of syloid. Appropriate coatings may be applied to increase palatability or delay absorption. A specific therapeutic formulation of the pharmaceutical composition described herein is set forth in the table below:

| Ingredient | Weight Percent (% w/w) | Amount (mg) | Chemical or Scientific Name (if different) |
|---|---|---|---|
| N-Acetylglucosamine | 17.1 | 140 | N-Acetyl D-Glucosamine |
| Vitamin C (81.2% Ascorbic Acid) | 15 | 123.2 | |
| L-Lysine (80%) | 12.2 | 100 | L-Lysine hydrochloride |
| L-Proline | 11 | 90 | |
| D-Glucosamine Sulfate (75%) | 6.5 | 53.3 | |
| Chondroitin Sulfate (80%) | 6.1 | 50 | |
| Vitamin E Succinate | 4.3 | 39.7 | D-α tocopheryl acid succinate |
| Zinc monomethionine (20% Zn) | 3.7 | 30 | Zinc DL-methionine |
| N-Acetyl Cysteine | 3.7 | 30 | |
| Manganese Ascorbate (13% Mn) | 2.8 | 23.1 | |
| Vitamin $B_3$ Niacinamide | 2.4 | 20 | Niacinamide |
| Quercetin Powder | 2.4 | 20 | Quercetin dihydrate |
| Grape Seed Extract | 0.9 | 7.5 | Proanthocyanidin |
| Pyridoxal 5 Phosphate-Co $B_6$ | 0.6 | 5 | P-5-P monohydrate |
| Selenomethionine (0.5%) | 0.5 | 4 | L-selenomethionine |
| Vitamin A Palmitate (500,000 IU/GR) | 0.5 | 4 | |
| Copper Sebacate (14%) | 0.4 | 2.9 | |
| Red beet root powder | 6.1 | 50 | Beta vulgaris rubra |
| Stearic acid | 1.5 | 12 | |
| Sorbitol | 1.3 | 11 | |
| Acdisol | 0.4 | 3 | Microcrystalline cellulose |
| Coconut oil | 0.1 | 1 | Magnesium stearate |
| Syloid | 0.1 | 1 | Silicon dioxide (amorphous) |
| Total | 100 | 820.7 | |

These tablets are an example of a tablet useful in the methods of the invention.

Example 4

Promotion of Hair Growth in Test Subjects

A 67 year-old female patient was administered the formulation described in Example 3 at a dose of 2 tablets (1641.4 mg) per day. After 2 months the patient reported increased hair growth on her toes and knees.

A 55 year-old female patient was administered the formulation described in Example 3 at a dose of 2 tablets (1641.4 mg) per day. After 3 months the patient reported increased hair growth on her toes.

A 40 year-old female patient was administered the formulation described in Example 3 at a dose of 2 tablets (1641.4 mg) per day. After 3 months the patient reported increased hair growth on her legs and forearms.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference in their entireties.

What is claimed is:

1. A method of promoting hair growth, which comprises: identifying an individual suffering from hair loss, and administering to the individual an effective amount for promoting hair growth of a composition comprising:
   (1) a sugar compound that is converted to a glycosaminoglycan in the patient;
   (2) a primary antioxidant component;
   (3) at least one amino acid component; and
   (4) at least one transition metal component,
   wherein the sugar compound is administered at a dose of from about 40 mg to about 2500 mg per day; the primary antioxidant is administered at a dose of from about 40 mg to about 2400 mg per day; the amino acid is administered at a dose of from about 35 mg to about 1200 mg per day; and the transition metal component is administered at a dose of from about 4.1 mg to about 740 mg per day,
   wherein the sugar compound and primary antioxidant component and at least one amino acid component and at least one transition metal component are administered simultaneously.

2. The method of claim 1, wherein the administration is topical.

3. The method of claim 1, wherein the administration is oral.

4. The method of claim 1, wherein the sugar compound and primary antioxidant component and at least one amino acid component and at least one transition metal component are administered simultaneously between 1 and 6 times per day.

5. The method of claim 4, wherein the sugar compound and primary antioxidant component and at least one amino acid component and at least one transition metal component are administered simultaneously 1 time per day.

6. A method of promoting hair growth, which comprises: identifying an individual suffering from hair loss, and administering to the individual an effective amount for promoting hair growth of a composition comprising:
   (1) a sugar compound that is converted to a glycosaminoglycan in the patient;
   (2) a primary antioxidant component;
   (3) at least one amino acid component; and
   (4) at least one transition metal component,
   wherein the sugar compound that is converted to a glycosaminoglycan in the patient; the primary antioxidant component; the at least one amino acid component; and the at least one transition metal component are administered as a pharmaceutical composition comprising:
   (1) a sugar compound that is converted to a glycosaminoglycan in the patient in an amount from about 5 to about 50 weight percent of the pharmaceutical composition;
   (2) a primary antioxidant component in an amount from about 5 to about 50 weight percent of the pharmaceutical composition;
   (3) at least one amino acid component in an amount from about 2 to about 25 weight percent of the pharmaceutical composition; and
   (4) at least one transition metal in an amount from about 0.5 to about 15 weight percent of the pharmaceutical composition
   wherein the sugar compound that is converted to a glycosaminoglycan in the patient is N-acetylglucosamine or a salt or ester thereof; the primary antioxidant component is ascorbic acid or a salt or ester thereof, the at least one amino acid is selected from the group consisting of proline, lysine, cysteine, and methionine; and the transition metal component is selected from the group consisting of zinc, manganese, copper, and mixtures thereof.

7. The method of claim 6, wherein the transition metal component is selected from the group consisting of zinc monomethionine, manganese ascorbate, and copper sebacate.

8. The method of claim 7, wherein the N-acetylglucosamine or salt or ester thereof; the ascorbic acid or salt or ester thereof; the at least one amino acid component; and either the zinc monomethionine, the manganese ascorbate, or the copper sebacate are administered as a pharmaceutical composition comprising:
   (1) N-acetylglucosamine or a salt or ester thereof in an amount from about 5 to about 50 weight percent;
   (2) ascorbic acid or a salt or ester thereof in an amount from about 5 to about 50 weight percent;
   (3) at least one amino acid component in an amount from about 4 to about 25 weight percent;
   (4) zinc monomethionine, if present, in an amount from about 1 to about 10 weight percent;
   (5) manganese ascorbate, if present, in an amount from about 1 about 10 weight percent; and
   (6) copper sebacate, if present, in an amount from about 0.1 to about 5 weight percent of the composition.

9. The method of claim 1, wherein the individual is suffering from alopecia wherein the administration.

* * * * *

UNITED STATES PATENT AND TRADEMARK OFFICE
CERTIFICATE OF CORRECTION

| | | |
|---|---|---|
| PATENT NO. | : 7,452,527 B2 | Page 1 of 1 |
| APPLICATION NO. | : 10/400795 | |
| DATED | : November 18, 2008 | |
| INVENTOR(S) | : Howard Murad | |

It is certified that error appears in the above-identified patent and that said Letters Patent is hereby corrected as shown below:

Column 14, Line 59-60, Claim 9, Should Read:
9. The method of claim 1, wherein the individual is suffering from alopecia wherein the administration is oral.

Signed and Sealed this

Twentieth Day of January, 2009

JON W. DUDAS
*Director of the United States Patent and Trademark Office*